(12) United States Patent
Ueda et al.

(10) Patent No.: US 7,981,309 B2
(45) Date of Patent: Jul. 19, 2011

(54) METHOD FOR DETECTING POLISHING END IN CMP POLISHING DEVICE, CMP POLISHING DEVICE, AND SEMICONDUCTOR DEVICE MANUFACTURING METHOD

(75) Inventors: Takehiko Ueda, Yokohama (JP); Hosei Nakahira, Tokyo (JP); Akira Ishikawa, Kawasaki (JP)

(73) Assignee: Nikon Corporation, Tokyo (JP)

( * ) Notice: Subject to any disclaimer, the term of this patent is extended or adjusted under 35 U.S.C. 154(b) by 559 days.

(21) Appl. No.: 11/921,008

(22) PCT Filed: May 16, 2006

(86) PCT No.: PCT/JP2006/309702
§ 371 (c)(1),
(2), (4) Date: Nov. 26, 2007

(87) PCT Pub. No.: WO2006/126420
PCT Pub. Date: Nov. 30, 2006

(65) Prior Publication Data
US 2009/0233525 A1    Sep. 17, 2009

(30) Foreign Application Priority Data
May 26, 2005   (JP) ................................. 2005-154303

(51) Int. Cl.
*C03C 25/68* (2006.01)
*B24B 49/00* (2006.01)

(52) U.S. Cl. ............................................. 216/84; 451/5

(58) Field of Classification Search .................. 216/84, 216/85, 88, 89; 451/6, 5, 41; 438/14, 7, 438/8, 16, 691–693; 700/266; 702/170; 257/E21.521
See application file for complete search history.

(56) References Cited

U.S. PATENT DOCUMENTS

| | | | |
|---|---|---|---|
| 6,932,671 B1 * | 8/2005 | Korovin et al. | 451/5 |
| 2002/0155788 A1 * | 10/2002 | Bibby et al. | 451/6 |
| 2004/0030060 A1 * | 2/2004 | Sunkara et al. | 525/453 |
| 2006/0030060 A1 * | 2/2006 | Noguchi et al. | 438/14 |

FOREIGN PATENT DOCUMENTS

| | | |
|---|---|---|
| JP | 2000-040680 | 2/2000 |
| JP | 2001-287159 | 10/2001 |

* cited by examiner

*Primary Examiner* — Nadine G Norton
*Assistant Examiner* — Patti Lin
(74) *Attorney, Agent, or Firm* — Finnegan, Henderson, Farabow, Garrett & Dunner, L.L.P.

(57) ABSTRACT

The spectral reflectance spectrum of an object of polishing that has reached the polishing endpoint is found ahead of time, the spectral reflectance spectrum of the object of polishing is found during polishing, and the correlation coefficient of these is seen as parameter 1. Meanwhile, the sum of the absolute values of the difference between the first order differentials of these is seen as parameter 2. Then, when parameter 1 is in a range exceeding a specific value, and parameter 2 is at its minimum, it is concluded that the polishing endpoint has been reached. Thus, it is possible to provide a method for detecting the polishing endpoint in a highly reliable CMP polishing apparatus.

12 Claims, 11 Drawing Sheets

METHOD FOR DETECTING POLISHING END IN CMP POLISHING DEVICE, CMP POLISHING DEVICE, AND SEMICONDUCTOR DEVICE MANUFACTURING METHOD

TECHNICAL FIELD

The present invention relates to a method for detecting the endpoint of polishing in a CMP polishing apparatus, a CMP polishing apparatus, and a semiconductor device manufacturing method.

BACKGROUND ART

The density of semiconductor devices continues to rise, with no end in sight, and the importance of technology for forming multilayer wiring and accompanying interlayer insulation films, or for forming plug, damascene, and other such electrodes becomes much greater as density increases. Naturally, a major concern is the monitoring of the thickness and shape of an interlayer insulation film or metal film (whether or not it is embedded or the like). The monitoring of film thickness is, of course, also necessary in the process of thin film formation or etching, but what has especially been viewed as a problem of late is the detection of the polishing endpoint in a planarization process.

An optical method is employed for such detection of the polishing endpoint. Specifically, the spectral reflectance spectrum at the polishing endpoint is found ahead of time for the wafer or other object of polishing, and when the spectral reflectance spectrum of the object of polishing as observed during polishing approaches the previously found spectral reflectance spectrum, it is concluded that the polishing endpoint has been reached. This method is described, for example, in Japanese Patent No. 3360610 (Patent Document 1).

[Patent Document 1] Japanese Patent No. 3360610

DISCLOSURE OF THE INVENTION

Problems to be Solved by the Invention

A method such as that described in Patent Document 1 affords good reliability as a method for detecting the polishing endpoint. However, in some cases, depending on the type of object of polishing, the observed spectral reflectance spectrum of the object of polishing may approach the previously found spectral reflectance spectrum while polishing is still underway, or conversely, even though the polishing endpoint is reached, the observed spectral reflectance spectrum of the object of polishing may not approach the previously found spectral reflectance spectrum due to the effect of noise or the like.

The present invention was devised in light of such circumstances, and it is an object of the present invention to provide a method for detecting the polishing endpoint in a highly reliable CMP polishing apparatus by a method different from what was considered in the past, and a CMP polishing apparatus that makes use of this method, as well as a method for manufacturing a semiconductor device using this CMP polishing apparatus.

Means for Solving the Problems

The first means used to solve the problems described above is a method for detecting the polishing endpoint in a CMP polishing apparatus, comprising the following steps:

(a) a step of finding in advance during CMP polishing the spectral reflectance spectrum of an object of polishing that has reached the polishing endpoint;

(b) a step of finding the spectral reflectance spectrum of an object of polishing within the duration of CMP polishing, and finding a correlation coefficient with the spectral reflectance spectrum of the object of polishing that has reached the polishing endpoint found in step (a);

(c) a step of finding, within the duration of CMP polishing, the sum of the absolute values of the difference at each wavelength, or the sum of the squares of the difference at each wavelength, between the first order differential with respect to the wavelength of the spectral reflectance spectrum found in step (a), and the first order differential with respect to the wavelength of the spectral reflectance spectrum found in step (b); and (d) a step of determining the polishing endpoint to be the point at which the sum of the absolute values of the difference at each wavelength, or the sum of the squares of the difference at each wavelength, found in step (c) is at the minimum value within a range in which the correlation coefficient found in step (b) is equal to or greater than a specific threshold.

In step (a), the spectral reflectance spectrum of an object of polishing that has reached the polishing endpoint is found in advance during CMP polishing by experimentation. The spectral reflectance spectrum of an object of polishing is affected by the wavelength distribution of the light source, the polishing liquid, and the like. Therefore, when this spectrum is to be found, it is found during the polishing work. For instance, the work of finding the spectral reflectance spectrum of the object of polishing is continued during polishing work, some other means is employed to find that the polishing endpoint has been reached, the spectral reflectance spectrum of the object of polishing at this point is stored, the object of polishing is taken out, and if the polishing endpoint has truly been reached, its spectral reflectance spectrum is employed; this work can be repeated over and over to find the answer by trial and error. Furthermore, the spectral reflectance spectrum is found for discrete wavelengths. For the sake of the following description, we shall let $f(\lambda)$ be the found spectral reflectance spectrum. $f(\lambda)$ is the spectral intensity when the wavelength is $\lambda$.

In step (b), the spectral reflectance spectrum of the object of polishing is measured during the polishing step. This spectral reflectance spectrum is affected by the wavelength distribution of the light source, the polishing liquid, and the like. For the sake of the following description, we shall let $g(\lambda)$ be the measured spectral reflectance spectrum. $g(\lambda)$ is the spectral intensity when the wavelength is $\lambda$. Then, the correlation coefficient between $f(\lambda)$ and $g(\lambda)$ is found. A cross-correlation coefficient is the correlation coefficient when $g(\lambda)$ is regressed with $f(\lambda)$, and refers to a regression coefficient a in cases where first-order regression is performed as follows:

$$g(\lambda) = a \cdot f(\lambda) + b$$

As the polishing proceeds, the regression coefficient steadily approaches 1 while fluctuating up and down. If $f(\lambda)$ perfectly matches $g(\lambda)$, the result is 1. Naturally, $f_m(\lambda)$ may also be regressed with $g_n(\lambda)$.

In step (c), either $$\int_\alpha^\beta \left| \frac{df(\lambda)}{d\lambda} - \frac{dg(\lambda)}{d\lambda} \right| d\lambda$$

or $$\int_\alpha^\beta \left( \frac{df(\lambda)}{d\lambda} - \frac{dg(\lambda)}{d\lambda} \right)^2 d\lambda$$

is found during the polishing step. Furthermore, α and β are the lower limit and upper limit to the wavelength used in the calculation. For example, the smaller of the wavelengths λ can be used for α, and the larger of the wavelengths can be used for β. In actuality, since the data that are employed are discrete, these data are preferably fitted to the functions f(λ) and g(λ), respectively, which are smooth function forms, and these are subjected to first order differentiation. In cases where the data do not fit the functions, these first order differentials are found as differences by numerical calculation, and the integrals described above are found as integration values. These values are unstable at the early stage of polishing, but undergo a monotone decrease as polishing proceeds, reaching their minimum at the polishing endpoint, and then changing to an increase. The reason for taking the difference in the first order differentials of the spectral reflectance spectrum is as follows: namely, when the difference is taken for spectral reflectance spectra, an offset may be produced in the spectral reflectance spectra depending on the condition of the polishing liquid or the like, and this may produce error, but this offset can be eliminated by taking a first order differential.

In step (d), the polishing endpoint is determined to be the point at which the sum of the absolute values of the difference at each wavelength, or the sum of the squares of the difference at each wavelength, found in step (c) is at the minimum value, within a range in which the correlation coefficient found in step (b) is equal to or greater than a specific threshold. As was described above, the correlation coefficient found in step (b) tends to rise as polishing proceeds, and to approach 1. However, there are cases in which the correlation coefficient may reach the maximum value even prior to the polishing endpoint, and therefore may not be well suited to direct use in determining the polishing endpoint. Accordingly, the correlation coefficient is used in determining that the polishing endpoint is approaching when this correlation coefficient has exceeded a specific threshold.

In contrast, the sum of the absolute values of the difference at each wavelength, or the sum of the squares of the difference at each wavelength, found in step (c) is unstable in the early stage of polishing, but undergoes a monotone decrease once the polishing proceeds a certain amount, and reaches its minimum at the polishing endpoint. Thus, as was described above, if it is known that the sum of the absolute values of the difference at each wavelength, or the sum of the squares of the difference at each wavelength, found in step (c) has entered a region (near the polishing endpoint) of monotone decrease from the fact that the correlation coefficient exceeds a threshold, and if these values have reached their minimum within that range, the polishing endpoint can be determined accurately.

The second means used to solve the problems described above is the first means, wherein in step (c), smoothing is performed after the first order differentials are found, and these smoothed values are used in calculating the sum of the absolute values of the difference at each wavelength, or the sum of the squares of the difference at each wavelength.

In performing first order differentiation, there are cases in which the value of the first order differential varies greatly due to minute noise or the like. In such cases, it is desirable that the first order differentials that are found be smoothed and used. Any universally known smoothing means can be employed, such as a moving average method or exponential smoothing method.

The third means used to solve the problems described above is a method for detecting the polishing endpoint in a CMP polishing apparatus, comprising the following steps:

(a) a step of finding in advance during CMP polishing a plurality of spectral reflectance spectra of objects of polishing undergoing polishing, along with the spectral reflectance spectrum of an object of polishing that has reached the polishing endpoint;

(b) a step of finding the spectral reflectance spectrum of an object of polishing within the duration of CMP polishing, and finding a correlation coefficient between the spectral reflectance spectrum of the object of polishing that has reached the polishing endpoint found in step (a), and the spectral reflectance spectrum of the object of polishing undergoing the polishing step; and (c) a step of determining the polishing endpoint to be the point at which the correlation coefficient with the previously found spectral reflectance spectrum of the object of polishing that has reached the polishing endpoint, out of the correlation coefficients found in step (b), becomes higher than the correlation coefficient with the spectral reflectance spectrum of another object of polishing undergoing polishing.

In the present means, a plurality of spectral reflectance spectra of the object of polishing undergoing polishing are found ahead of time during CMP polishing in step (a), along with the spectral reflectance spectrum of the object of polishing that has reached the polishing endpoint. For example, we will let the spectral reflectance spectra found for the object of polishing to be $f_1(\lambda), f_2(\lambda), \ldots, f_k(\lambda)$, in the order of polishing progress, and let $f_k(\lambda)$ be the spectral reflectance spectrum of the polishing endpoint of the object of polishing.

In step (b), the spectral reflectance spectrum of the object of polishing is found just as in the first means described above. We will let this be $g(\lambda)$. The respective correlation coefficients between this $g(\lambda)$ and $f_1(\lambda), f_2(\lambda), \ldots, f_k(\lambda)$ are then found in the same way as in the first means.

In step (c), it is determined that the polishing endpoint has been reached when the correlation coefficient between $g(\lambda)$ and $f_k(\lambda)$ has become the largest of the respective correlation coefficients found in step (b). Specifically, $f_1(\lambda), f_2(\lambda), \ldots, f_{k-1}(\lambda)$ are the spectral spectra at points in time at which polishing has not yet been completed. Malfunction of polishing endpoint detection can be reduced by comparing $g(\lambda)$ with these spectral reflectance spectra at points prior to the completion of polishing.

The fourth means used to solve the problems described above is a method for detecting the polishing endpoint in a CMP polishing apparatus, comprising the following steps:

(a) a step of finding in advance during CMP polishing a plurality of spectral reflectance spectra of objects of polishing undergoing polishing, along with the spectral reflectance spectrum of an object of polishing that has reached the polishing endpoint;

(b) a step of finding the spectral reflectance spectrum of an object of polishing within the duration of CMP polishing, and finding a correlation coefficient between the spectral reflectance spectrum of the object of polishing that has reached the polishing endpoint found in step (a), and the spectral reflectance spectrum of the object of polishing undergoing the polishing step;

(c) a step of finding, within the duration of CMP polishing, the sum of the absolute values of the difference at each wavelength, or the sum of the squares of the difference at each wavelength, between the first order differential with respect to the wavelength of the spectral reflectance spectrum of the object of polishing that has reached the polishing endpoint found in step (a), and the first order differential with respect to the wavelength of the spectral reflectance spectrum found in step (b); and (d) a step of determining the polishing endpoint to be the point at which the correlation coefficient with the previously found spectral reflectance spectrum of the object of polishing that has reached the polishing endpoint becomes the highest out of the correlation coefficients found in step (b), and the sum of the absolute values of the difference at each wavelength, or the sum of the squares of the difference at each wavelength, found in step (c) is at the minimum value.

In the present means, step (a) and step (b) are the same as those in the third means. Furthermore, step (c) is the same as that in the first means. In step (d), the polishing endpoint is determined to be the point at which the correlation coefficient with the previously found spectral reflectance spectrum of the object of polishing that has reached the polishing endpoint becomes the highest out of the correlation coefficients found in step (b), and the sum of the absolute values of the difference at each wavelength, or the sum of the squares of the difference at each wavelength, found in step (c) is at the minimum value.

Specifically, the basic way of determining the polishing endpoint is the same as in the first means. However, the method used in the third means is employed to determine whether or not the sum of the absolute values of the difference at each wavelength, or the sum of the squares of the difference at each wavelength, found in step (c) has entered the stage of a monotone decrease. The polishing endpoint can also be found accurately by such a method.

The fifth means used to solve the problems described above is the fourth means, wherein in step (c), smoothing is performed after the first order differentials are found, and these smoothed values are used in calculating the sum of the absolute values of the difference at each wavelength, or the sum of the squares of the difference at each wavelength.

In the present means, the technological significance and effect of performing smoothing on the first order differentials are the same as those in the second means.

The sixth means used to solve the problems described above is any of the first through fifth means, and is a method for detecting the polishing endpoint in a CMP polishing apparatus, wherein a white LED is used as the light source for measuring the spectral reflectance spectrum, the current applied to this white LED is controlled at a constant value, and the amount of irradiating light is controlled using a variable ND filter so that the amount of reflected light from the object of polishing will fall within a specific range.

A white LED is an advantageous light source for spectral measurement because the spectrum distribution of the light source is stable. However, the spectrum distribution varies if the current applied in order to vary the amount of light is changed, so that this is a drawback to a method in which the time series behavior of a spectral reflectance spectrum is used as a parameter, as in this method. In view of this, a constant current is used in the present means. Meanwhile, in cases where the spectral reflectance spectrum of an object of polishing is measured during polishing with a CMP polishing apparatus, the amount of reflected light varies due to the influence of the slurry thickness and the like. When the amount of reflected light is smaller, in particular, the S/N ratio deteriorates. Therefore, the amount of received light is preferably controlled so as to fall within a specific range. Accordingly, in the present means, intense light is emitted from a white LED, the amount of this light is reduced with a variable ND filter, and the resulting light is used as the measurement light source. The amount of reflected light received from the object of polishing is then monitored, and the transmittance of the variable ND filter is adjusted so that this amount will be within a specific range.

The seventh means used to solve the problems described above is any of the first through fifth means, wherein a white LED is used as the light source for measuring the spectral reflectance spectrum, the current applied to this white LED is controlled so that the amount of reflected light from the object of polishing will fall within a specific range, and the spectral reflectance spectrum of the object of polishing attributable to the change in the emission spectrum of the white LED due to the change in the current applied to the white LED is compensated on the basis of the relationship between the applied current and the emission spectrum of the white LED as determined ahead of time.

The amount of reflected light received from the object of polishing may be monitored, and the current applied to a white LED may be varied in order to keep this amount within a specific range. As was mentioned above, however, a problem is that the emission spectrum distribution varies. In the present means, the relationship between the applied current and the emission spectrum of the white LED is determined ahead of time, the spectral reflectance spectrum actually obtained from the light reflected by the object of polishing is compensated on the basis of this relationship, and this is normalized for use. Thus, the polishing endpoint can be detected accurately even if the current applied to the white LED varies.

The eighth means used to solve the problems described above is any of the first through seventh means, wherein the spectral reflectance spectrum is the average value or integrated value over one rotation of the object of polishing undergoing CMP polishing.

In the present means, even if the polishing of the object of polishing is uneven, it can be averaged in the detection of the polishing endpoint.

The ninth means used to solve the problems described above is any of the first through eighth means, wherein the spectral reflectance spectrum of the object of polishing at a specific length of time prior to reaching the polishing endpoint is used instead of the spectral reflectance spectrum of the object of polishing that has reached the polishing endpoint.

In cases where an attempt is made to determine the polishing endpoint on the basis of the first or fourth means, in particular, it is necessary to determine the minimum point. In order to find whether or not the minimum point has been attained, it is necessary to continue acquiring data even after the minimum point has been passed, so that the point at which it can be concluded that the polishing endpoint has been reached is actually after the polishing endpoint has been passed. The present means is effective when this becomes a problem. Moreover, the lag in determination caused by averaging can also be corrected at the same time.

In the present means, the spectral reflectance spectrum of the object of polishing at a specific length of time prior to reaching the polishing endpoint is employed as a reference spectrum, rather than the spectral reflectance spectrum of the object of polishing that has reached the polishing endpoint. It is desirable that this specific length of time used be a value close to the time elapsed from when the minimum value appears until it can be concluded that this is the minimum value. If this is done, the polishing endpoint is actually reached at the point at which the value is determined to be the minimum value, so that the polishing can be accurately concluded at the polishing endpoint.

The tenth means used to solve the problems described above is a method for detecting the polishing endpoint in a CMP polishing apparatus, comprising the following steps:

(a) a step of performing over-polishing during CMP polishing after the polishing endpoint has been reached, and finding in advance the spectral reflectance spectrum of an object of polishing at one or a plurality of points during the over-polishing;
(b) a step of finding the spectral reflectance spectrum of an object of polishing during CMP polishing, and finding a correlation coefficient with any of the spectral reflectance spectra of the object of polishing during over-polishing as found in step (a); and
(c) a step of determining the polishing endpoint to be the point at which the correlation coefficient found in step (b) is equal to or greater than a specific threshold.

The eleventh means used to solve the problems described above is any of the first through fifth means, and is a method for detecting the polishing endpoint in a CMP polishing apparatus, wherein this method also has a polishing endpoint detection method comprising the following steps, and the polishing endpoint is determined to be the point at which the polishing endpoint is first detected in any of the polishing endpoint detection methods:
(a) a step of performing over-polishing during CMP polishing after the polishing endpoint has been reached, and finding in advance the spectral reflectance spectrum of an object of polishing at one or a plurality of points during the over-polishing;
(b) a step of finding the spectral reflectance spectrum of an object of polishing during CMP polishing, and finding a correlation coefficient with any of the spectral reflectance spectra of the object of polishing during over-polishing as found in step (a); and
(c) a step of determining the polishing endpoint to be the point at which the correlation coefficient found in step (b) is equal to or greater than a specific threshold.

The twelfth means used to solve the problems described above is a method for detecting the polishing endpoint in a CMP polishing apparatus, comprising the following steps:
(a) a step of finding in advance during CMP polishing the spectral reflectance spectrum of an object of polishing that has reached the polishing endpoint;
(b) a step of finding the spectral reflectance spectrum of an object of polishing during CMP polishing;
(c) a step of finding, within the duration of CMP polishing, the sum of the absolute values of the difference at each wavelength, or the sum of the squares of the difference at each wavelength, between the first order differential with respect to the wavelength of the spectral reflectance spectrum found in step (a), and the first order differential with respect to the wavelength of the spectral reflectance spectrum found in step (b); and
(d) a step of determining the polishing endpoint to be the point at which the sum of the absolute values of the difference at each wavelength, or the sum of the squares of the difference at each wavelength, found in step (c) becomes the minimum value.

The thirteenth means used to solve the problems described above is the twelfth means, and is a method for detecting the polishing endpoint in a CMP polishing apparatus, wherein steps (b), (c) and (d) are commenced after the elapse of the estimated time it takes to approach the polishing endpoint.

The fourteenth means used to solve the problems described above is a method for detecting the polishing endpoint in a CMP polishing apparatus, comprising the following steps:
(a) a step of finding in advance during CMP polishing the spectral reflectance spectrum of an object of polishing that has reached the polishing endpoint;
(b) a step of finding the spectral reflectance spectrum of an object of polishing during CMP polishing, and finding a first parameter which is obtained from this spectral reflectance spectrum and the spectral reflectance spectrum of the object of polishing that has reached the polishing endpoint found in step (a), and which approaches a normalized value (such as 1) toward the polishing endpoint;
(c) a step of finding, within the duration of CMP polishing, a second parameter which is obtained from the spectral reflectance spectrum found in step (a) and the spectral reflectance spectrum found in step (b), and which attains the minimum value at the polishing endpoint; and
(d) a step of determining the polishing endpoint to be the point at which the first parameter found in step (b) is in a range equal to or greater than a specific threshold, and the second parameter found in step (c) is at the minimum value.

The fifteenth means used to solve the problems described above is a method for detecting the polishing endpoint in a CMP polishing apparatus, comprising the following steps:
(a) a step of finding in advance during CMP polishing the spectral reflectance spectrum of an object of polishing that has reached the polishing endpoint;
(b) a step of finding the spectral reflectance spectrum of an object of polishing during CMP polishing, and finding a correlation coefficient with the spectral reflectance spectrum of the object of polishing that has reached the polishing endpoint as found in step (a);
(c) a step of finding, within the duration of CMP polishing, the sum of the absolute values of the difference at each wavelength, or the sum of the squares of the difference at each wavelength, between the first order differential with respect to the wavelength of the spectral reflectance spectrum found in step (a), and the first order differential with respect to the wavelength of the spectral reflectance spectrum found in step (b), within a range in which the correlation coefficient found in step (b) is equal to or greater than a specific threshold; and
(d) a step of determining the polishing endpoint to be the point at which the sum of the absolute values of the difference at each wavelength, or the sum of the squares of the difference at each wavelength, found in step (c) is at the minimum value.

The sixteenth means used to solve the problems described above is a CMP polishing apparatus having a polishing end determination device which finds the polishing endpoint of an object of polishing from the spectral reflectance spectrum of this object of polishing, wherein the polishing end determination device finds the polishing endpoint of the object of polishing by using any of the polishing endpoint detection methods in a CMP polishing apparatus from among the first through fifteenth means.

In the present means, polishing can be performed accurately because the polishing endpoint of the object of polishing can be accurately ascertained.

The seventeenth means used to solve the problems described above is a semiconductor device manufacturing method comprising a step of polishing a wafer using the CMP polishing apparatus constituting the sixteenth means.

In the present means, since accurate CMP polishing is possible, semiconductor devices having a microscopic structure can be manufactured at a high yield.

Effect of the Invention

The present invention can provide a method for detecting the polishing endpoint in a highly reliable CMP polishing apparatus, and a CMP polishing apparatus that makes use of this method, as well as a method for manufacturing a semiconductor device using this CMP polishing apparatus.

EXPLANATION OF SYMBOLS

1 . . . white LED, 2 . . . lens, 3 . . . variable ND filter, 4 . . . illuminated area control slit, 5 . . . lens, 6 . . . beam splitter, 7 . . . lens, 8 . . . measured wafer, 9 . . . lens, 10 . . . mirror, 11 . . . lens, 12 . . . slit, 13 . . . lens, 14 . . . diffraction grating, 15 . . . linear sensor, 21 . . . holder, 22 . . . polishing board, 23 . . . polishing body, 24 . . . polishing liquid supply part, 25 . . . polishing liquid, 26 . . . polishing endpoint detection apparatus, 27 . . . photodetector, 28 . . . cover, 31 . . . silicon substrate, 32 . . . oxidation film, 33 . . . low-k film, 34 . . . CAP layer, 35 . . . Ta/TaN layer, 36 . . . copper, 37 . . . trench part

BEST MODE FOR CARRYING OUT THE INVENTION

Figure 1:
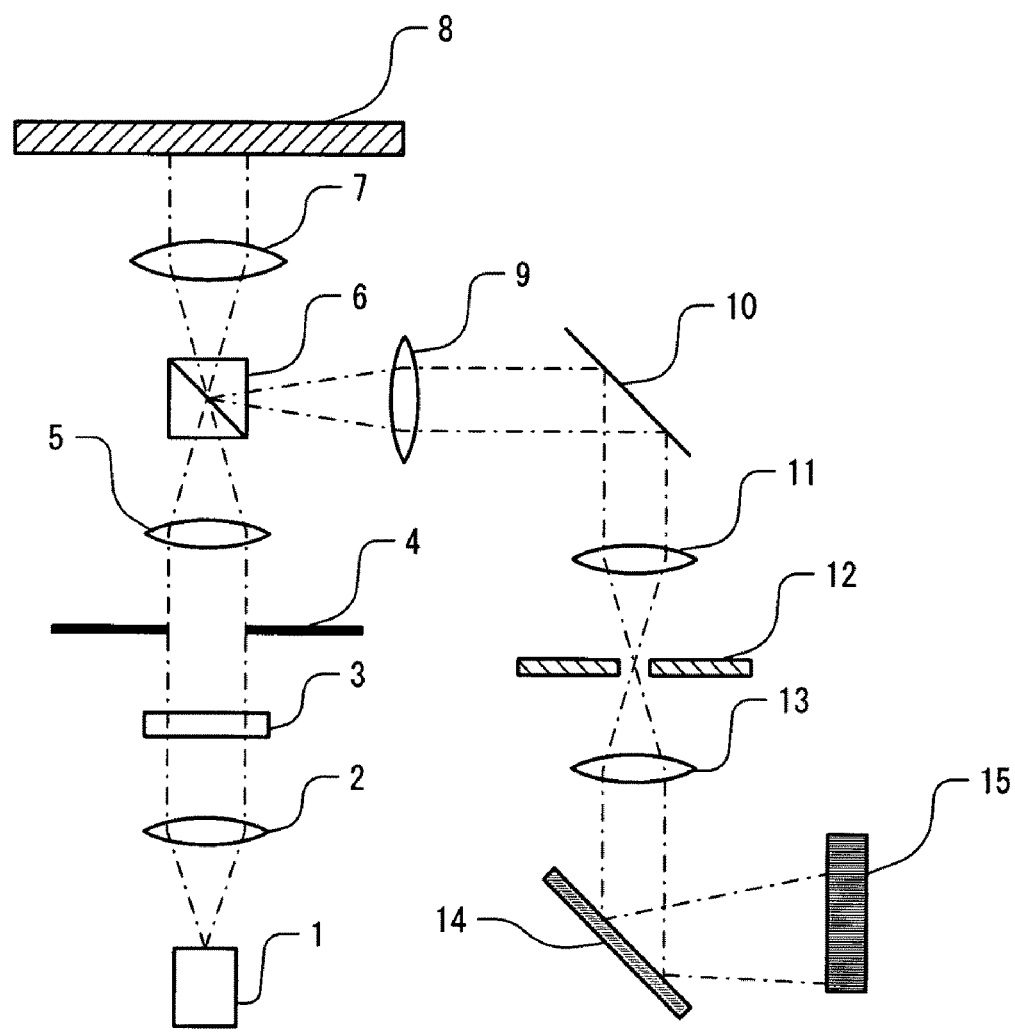
FIG. 1 is a diagram illustrating an example of the optical system of a CMP polishing endpoint detection apparatus that makes use of the method for detecting the polishing endpoint in a CMP polishing apparatus constituting a working configuration of the present invention.

Working configurations of the present invention will be described below using the figures. FIG. 1 is a diagram illustrating an example of the optical system of a CMP polishing endpoint detection apparatus that makes use of the method for detecting the polishing endpoint in a CMP polishing apparatus constituting a working configuration of the present invention.

Light from a white LED 1 constituting the light source is converted into a parallel light beam by a lens 2, passes through a variable ND filter 3 and an illuminated area control slit 4, and is then converged on a beam splitter 6 by a lens 5. The light that has passed through the beam splitter 6 is again made into a parallel beam by a lens 7, and irradiates the surface of a measured wafer 8 constituting the object of polishing.

The light reflected by the measured wafer 8 passes through the lens 7 again and is converged on the beam splitter 6. In the beam splitter 6, the direction of the reflected light is changed by 90°, and the light is made into a parallel beam by a lens 9. The light is then reflected by a mirror 10, and is converged by a lens 11 on a slit 12 which constitutes a light blocking means and which has an opening that selects only zero-order light. Scattered light, diffracted light, and other noise components are then removed, and the light goes through a lens 13 and is projected on and separated by a diffraction grating 14 constituting a light separation means. The separated light is incident on a linear sensor 15 constituting a photoelectric conversion element, and the spectral intensity is measured.

In this optical system, an image of the white LED 1 is formed on the beam splitter 6, and this imaging position is located at the front focal point of the lens 7. Accordingly, the surface of the measured wafer 8 is irradiated evenly and by a substantially perpendicular, parallel light beam. Moreover, the slit 12 is provided at the convergence position of the perpendicular, reflected light from the measured wafer 8. Therefore, the NA of the reflected light, i.e., the reflection angle of the light passing through the opening, can be adjusted by adjusting the diameter of this opening. Furthermore, in cases where the beam splitter 6 is a polarized beam splitter, a λ/4 plate is inserted between the lens 7 and the measured wafer 8.

Figure 2:
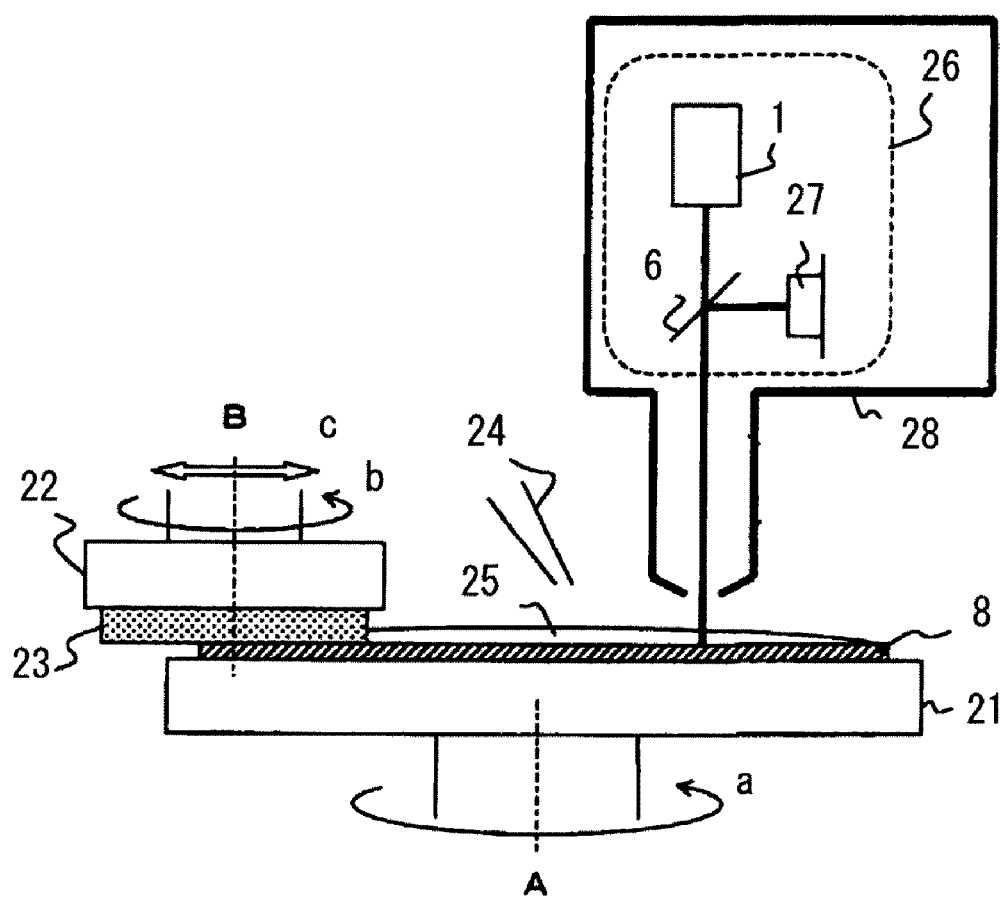
FIG. 2 is a diagram illustrating the relationship between a polishing endpoint detection apparatus having the optical system shown in FIG. 1 and an actual CMP polishing apparatus.

FIG. 2 illustrates the relationship between a polishing endpoint detection apparatus having an optical system such as this and an actual CMP polishing apparatus. In FIG. 2, those constituent elements that are the same as the constituent elements shown in FIG. 1 are labeled with the same symbols, and a description of such constituent elements is omitted. 21 is a component for holding the object of polishing (hereinafter referred to as a holder), 22 is a polishing board, 23 is a polishing body, 24 is a polishing liquid supply part, 25 is a polishing liquid (slurry), 26 is a polishing endpoint detection apparatus, 27 is a photodetector, and 28 is a cover. The photodetector 27 is depicted as part of the optical system in FIG. 1 through which the light passes after being reflected by the beam splitter 6.

The main body of the polishing apparatus is constituted by the holder 21, the polishing board 22, the polishing body 23 that is affixed to the polishing board 22, and the polishing liquid supply part 24. The measured wafer 8 constituting the object of polishing is attached to the holder 21, and polishing liquid 25 is supplied by the polishing liquid supply part 24.

A sheet-form polishing pad composed of polyurethane foam, or a polishing pad of an unfoamed resin having a groove structure on the surface, is used as the polishing body 23. The holder 21 is rotated in the direction of the arrow a around the axis A by a suitable means, and the polishing board 22 is rotated in the direction of the arrow b around the axis B by a suitable means. Furthermore, the axis B swings as indicated by the arrow c so that it moves linearly closer to or away from the axis A. In the course of all this, the polishing surface of the measured wafer 8 (the surface in contact with the polishing body 23) is polished by the action of the polishing liquid 25 and polishing body 23.

The polishing endpoint measurement apparatus 26 is installed above the measured wafer 8. The polishing endpoint measurement apparatus 26 is substantially covered by the cover 28 in order to prevent the polishing liquid from splattering onto the polishing endpoint determination apparatus 26.

In the figure, only the white LED light source 1, the beam splitter 6, and the photodetector 27 are shown as the constituent elements of the polishing endpoint determination apparatus 26, and illustration of the details is omitted, but the actual optical system of the polishing endpoint determination apparatus 26 used is the one shown in FIG. 1.

A working configuration of the method for determining the polishing endpoint using a polishing endpoint determination apparatus structured as described above will be described below. This method is actually carried out mainly by a computer built into the polishing endpoint determination apparatus 26.

In the first working configuration, the spectral reflectance spectrum of the measured wafer which will serve as a reference for determining the polishing endpoint is first acquired. Since the spectral reflectance spectrum to be compared is measured during the polishing step, a spectral reflectance spectrum that will serve as a reference must also be acquired during the polishing step. This may be accomplished by determining one way or another (such as from the elapsed polishing time) that the polishing endpoint is near, and concluding the polishing when the spectral reflectance spectrum of the measured wafer at that point is acquired. This is carried out for a plurality of measured wafers (changing the elapsed polishing time slightly each time, for example), the result that is closest to the end polishing state is selected, and the spectral reflectance spectrum corresponding to that result may be employed as a reference.

The "spectral reflectance spectrum" referred to in this specification, as can be understood from the above description, is the spectral reflectance spectrum in a polishing state, and is therefore affected by the spectral transmittance of the slurry or the like. This may be the physical spectral reflectance spectrum, i.e., the spectral reflectance spectrum when illumination is performed with completely white light, or it may be the spectral reflectance spectrum when illumination is performed with a light source having a specific spectrum distribution (that is, the spectrum is affected by the light source). In the latter case, the obtained spectrum distribution can be used just as it is. In the former case, the obtained spectrum distribution must be normalized with the spectrum distribution of the light source. We will let $f(\lambda)$ be the obtained spectral reflectance spectrum distribution. $\lambda$ is the wavelength, and is a discrete value.

After this preparation is complete, and when the wafer is actually polished, the spectral reflectance spectrum of this wafer is measured. We will let the obtained spectral reflectance spectrum distribution be $g(\lambda)$. $\lambda$ is the wavelength, and is a discrete value. Usually, it is desirable that the $\lambda$ when $f(\lambda)$ is measured and the $\lambda$ when $g(\lambda)$ is measured be the same wavelength in all cases.

In cases where the spectral reflectance spectrum distribution $g(\lambda)$ is obtained, a correlation coefficient between this and the spectral reflectance spectrum $f(\lambda)$ that serves as a reference is found. Correlation coefficients are widely used for statistical purposes, and here the correlation coefficient refers to a regression coefficient a when first-order regression is performed as follows:

$$g(\lambda) = a \cdot f(\lambda) + b$$

As the polishing proceeds, the regression coefficient steadily approaches 1 while fluctuating up and down. If $f(\lambda)$ perfectly matches $g(\lambda)$, the result is 1.

At the same time with this, the absolute value of the difference between the first order differential with respect to the $\lambda$ of the obtained spectral reflectance spectrum $g(\lambda)$ and the first order differential with respect to the $\lambda$ of the spectral reflectance spectrum $f(\lambda)$ serving as a reference is integrated with the wavelength band of the measurement range, or the square of the absolute value of the difference between the first order differential with respect to the $\lambda$ of the obtained spectral reflectance spectrum $g(\lambda)$ and the first order differential with respect to the $\lambda$ of the spectral reflectance spectrum $f(\lambda)$ serving as a reference is integrated with the wavelength band of the measurement range. One method for finding the first order differential is to fit $f(\lambda)$ and $g(\lambda)$ into smooth function forms $f(\lambda)$ and $g(\lambda)$, respectively, and find the first order differential thereof, and other method is to find the first order differential from the difference obtained by numerical calculation. In the case of the latter, however, hunting may occur due to minute noise, so that the former is preferable. In cases where the latter method is employed, the obtained first order differential is preferably used after being smoothed by using a moving average, exponential smoothing, or the like with respect to the $\lambda$. We will let the value found in this manner be c.

When the correlation coefficient (regression coefficient) a thus found is equal to or greater than a specific value, and the value of c is at its minimum, it is concluded that the endpoint of polishing has been reached. This allows the polishing endpoint to be detected accurately. Furthermore, if the above-mentioned measurement of the spectral reflectance spectrum of the wafer undergoing polishing, or the attendant determination processing, does not have to be performed in all of the polishing steps, and the polishing time up to the polishing endpoint can be more or less estimated, then such measurement or determination processing may be commenced after the time until the polishing endpoint is approached has elapsed.

In the second working configuration, just as in the first working configuration, the spectral reflectance spectrum of the measured wafer that will serve as a reference for determining the polishing endpoint is first acquired, and along with this, a plurality of spectral reflectance spectra of the measured wafer are measured at suitable intervals in the course of polishing (not necessarily at constant intervals). We will let the spectral reflectance spectra thus found for the object of polishing be $f_1(\lambda), f_2(\lambda), \ldots, f_k(\lambda)$, in the order of how the polishing proceeds, and let $f_k(\lambda)$ be the spectral reflectance spectrum at the polishing endpoint of the object of polishing.

In the actual polishing of a wafer, just as in the first working configuration, the spectral reflectance spectrum of the object of polishing is found. We will let this be $g(\lambda)$. The respective correlation coefficients between this $g(\lambda)$ and $f_1(\lambda)$, $f_2(\lambda), \ldots, f_k(\lambda)$ are then found in the same manner as in the first working configuration. Then, it is determined that the polishing endpoint has been reached when the correlation coefficient between $g(\lambda)$ and $f_k(\lambda)$ has become the largest of the correlation coefficients that are found. Even if the correlation coefficient between $g(\lambda)$ and $f_i(\lambda)$ ($i \neq k$) should become large, endpoint determination is not performed because $f_i(\lambda)$ is not the spectrum at the true polishing endpoint.

In the third working configuration, just as in the first working configuration, the spectral reflectance spectrum of the measured wafer that will serve as a reference for determining the polishing endpoint is first acquired, and along with this, a plurality of spectral reflectance spectra of the measured wafer are measured at suitable intervals in the course of polishing (not necessarily at constant intervals). We will let the spectral reflectance spectra thus found for the object of polishing be $f_1(\lambda), f_2(\lambda), \ldots, f_k(\lambda)$, in the order of how the polishing proceeds, and let $f_k(\lambda)$ be the spectral reflectance spectrum at the polishing endpoint of the object of polishing.

In the actual polishing of a wafer, just as in the first working configuration, the spectral reflectance spectrum of the object of polishing is found. We will let this be $g(\lambda)$. The respective correlation coefficients between this $g(\lambda)$ and $f_1(\lambda)$, $f_2(\lambda), \ldots, f_k(\lambda)$ are then found in the same manner as in the first working configuration. The above steps are the same as in the second working configuration.

At the same time with this, just as in the first working configuration, the absolute value of the difference between the first order differential with respect to the $\lambda$ of the obtained spectral reflectance spectrum $g(\lambda)$ and the first order differential with respect to the $\lambda$ of the spectral reflectance spectrum $f(\lambda)$ serving as a reference is integrated with the wavelength band of the measurement range, or the square of the absolute value of the difference between the first order differential with respect to the $\lambda$ of the obtained spectral reflectance spectrum $g(\lambda)$ and the first order differential with respect to the $\lambda$ of the spectral reflectance spectrum $f(\lambda)$ serving as a reference is integrated with the wavelength band of the measurement range. We will let this value be c.

Then, it is determined that the polishing endpoint has been reached when the correlation coefficient between $g(\lambda)$ and $f_k(\lambda)$ has become the largest of the respective correlation coefficients between $g(\lambda)$ and $f_1(\lambda), f_2(\lambda), \ldots, f_k(\lambda)$, and the value of c is at its minimum.

Of the working configurations described above, in the first working configuration and third working configuration, in particular, determination of the minimum value is performed. It cannot be determined that the minimum value has been reached until the determined value increases again; furthermore, if an attempt is made to avoid the effect of noise, it will be necessary to wait until an increase to or over a specific value is recognized. Accordingly, the point at which it is concluded that the minimum has been reached is a specific length of time after the point at which the minimum is reached. This lag time usually poses no problems, but if it should be a problem, it is sufficient if the reference spectral reflectance spectrum is seen not as the spectral reflectance spectrum at the polishing endpoint, but rather as the spectral reflectance spectrum at a point earlier by the above-mentioned lag time. Doing this allows the polishing endpoint to be reached exactly at the point at which it is concluded that the minimum has been reached. The same concept can also be applied to the second working configuration.

In the working configurations described above, the intensity of the reflected light from the measured wafer 8 has to be high enough for the spectral reflectance spectrum to be measured in a good S/N state. The intensity observed with the light receiving optical system varies with the thickness of the polishing liquid 25 and the like, and in some cases, a sufficient amount of light may not be received. To prevent such situations, the emission intensity of the white LED 1 is raised, the applied current is held constant, and in an ordinary state, the variable ND filter 3 is used to reduce the amount of light irradiating the measured wafer 8. Then, for example, the light that has passed through the lens 9 is split in two by a half-mirror or the like, half of which is guided to a light receiving element, and the transmittance of the variable ND filter 3 is adjusted so that the output of this light receiving element will fall within a specific range (or be constant). If this is done, the reflected light received by the light receiving optical system can be kept within a specific range (or constant), without changing the current applied to the white LED 1.

One possible way to keep the reflected light received by the light receiving optical system within a specific range (or constant) is to change the emission intensity by adjust the current applied to the white LED 1 However, doing this is undesirable because the emission spectrum of the white LED 1 will vary. Accordingly, in cases where a method such as this is employed, it is necessary to examine in advance the relationship between the applied current and the emission spectrum, and to normalize the detected spectral reflectance spectrum of the measured wafer 8 with the emission spectrum corresponding to the applied current.

In the fourth working configuration, in acquiring the spectral reflectance spectrum ahead of time, over-polishing is performed after the polishing endpoint has been passed, and the spectral reflectance spectrum after the polishing endpoint has been passed is acquired ahead of time. Furthermore, in determining the polishing endpoint, a correlation coefficient is found for the spectral reflectance spectrum measured during actual polishing and the previously acquired spectral reflectance spectrum following the polishing endpoint, and once this correlation coefficient reaches a specific value (a preset threshold), it is concluded that the polishing endpoint has been reached, and polishing is immediately halted. The previously acquired spectral reflectance spectrum following the polishing endpoint that is used to determine the polishing endpoint may be a single spectrum or two or more spectra.

The fourth working configuration is effective when used in combination with any of the first through third working configurations. Specifically, when the polishing rate is extremely high, there is the risk in all of the first through third working configurations that the polishing endpoint will not be properly determined, and polishing will not be halted, resulting in over-polishing. However, if the fourth working configuration is used in combination with these working configurations, over-polishing can be prevented because the polishing endpoint can be determined in the fourth working configuration even in cases where the polishing endpoint cannot be properly determined with the first through third working configurations.

In the CMP polishing apparatus shown in FIG. 2, the diameter of the polishing body 23 is smaller than the diameter of the measured wafer 8, and the surface of the measured wafer is facing up. Accordingly, in cases where the polishing endpoint detection apparatus 26 is installed in a specific position, the spectral reflectance spectrum can be measured over one full rotation at the same radius. Thus, if these spectral reflectance spectra of one rotation each are averaged or integrated before use, the effect of polishing unevenness at different places and the effect of diffraction caused by a pattern can be completely eradicated theoretically.

Figure 3:
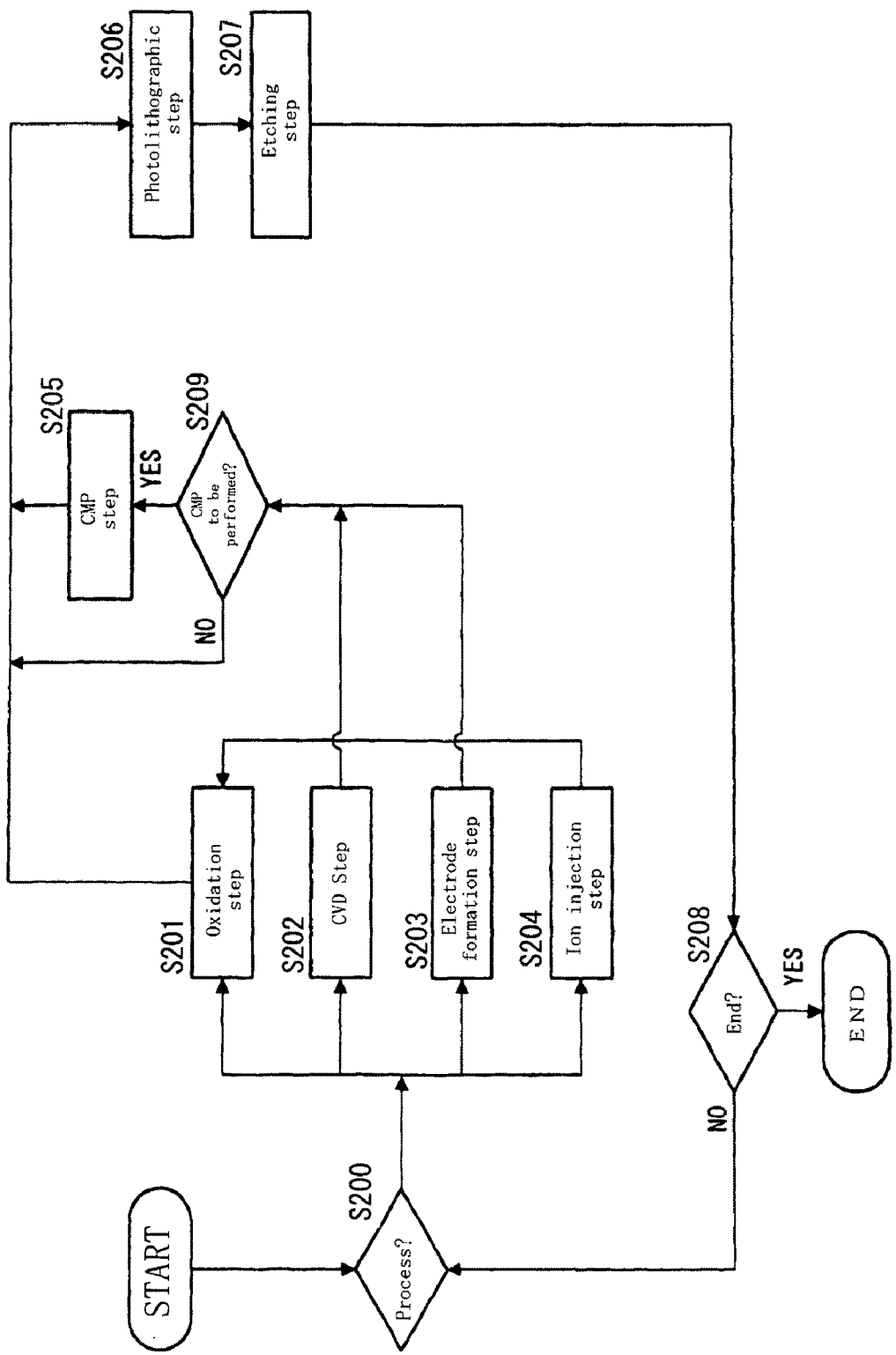
FIG. 3 is a diagram showing the semiconductor device manufacturing method that constitutes a working configuration of the present invention.

FIG. 3 is a diagram showing a semiconductor device manufacturing method constituting a working configuration of the present invention. When the semiconductor device manufacturing process is started, the appropriate treatment process is first selected in step S200 from the following steps S201 through S204. Then, the processing proceeds to one of the steps.

Here, step S201 is an oxidation process in which the surface of the wafer is oxidized. Step S202 is a CVD process in which an insulating film or dielectric film is formed on the surface of the wafer by CVD or the like. Step S203 is an electrode formation process in which electrodes are formed on the wafer by vacuum evaporation or the like. Step S204 is an ion injection process in which ions are injected into the wafer.

Following the CVD process (S202) or electrode formation process (S203), the processing proceeds to step S205. Step S205 is a CMP process. In the CMP process, the planarization of interlayer insulating films, the formation of a damascene by the polishing of a metal film or the polishing of a dielectric film on the surface of the semiconductor device, and the like are performed using the polishing apparatus according to the present invention.

Following the CMP process (S205) or oxidation process (S201), the processing proceeds to step S206. Step S206 is a photolithographic process. In this process, the coating of the wafer with a resist, the burning of a circuit pattern onto the wafer by exposure using an exposure apparatus, and the development of the exposed wafer are performed. Furthermore, the subsequent step S207 is an etching process in which the portions other than the developed resist image are removed by etching, the resist is then stripped away, and the unnecessary resist following the completion of etching is removed.

Next, in step S208, a judgment is made as to whether or not all of the required processes have been completed. If the processes have not been completed, the processing returns to step S200, and the preceding steps are repeated so that a circuit pattern is formed on the wafer. If it is judged in step S208 that all of the processes have been completed, the processing is ended.

In the semiconductor device manufacturing method according to the present invention, since the CMP polishing apparatus of the present invention is used in the CMP process, wafers having fine patterns can be polished accurately, so that semiconductor devices having a more favorable performance can be manufactured.

EMBODIMENTS

Embodiment 1

Figure 4:
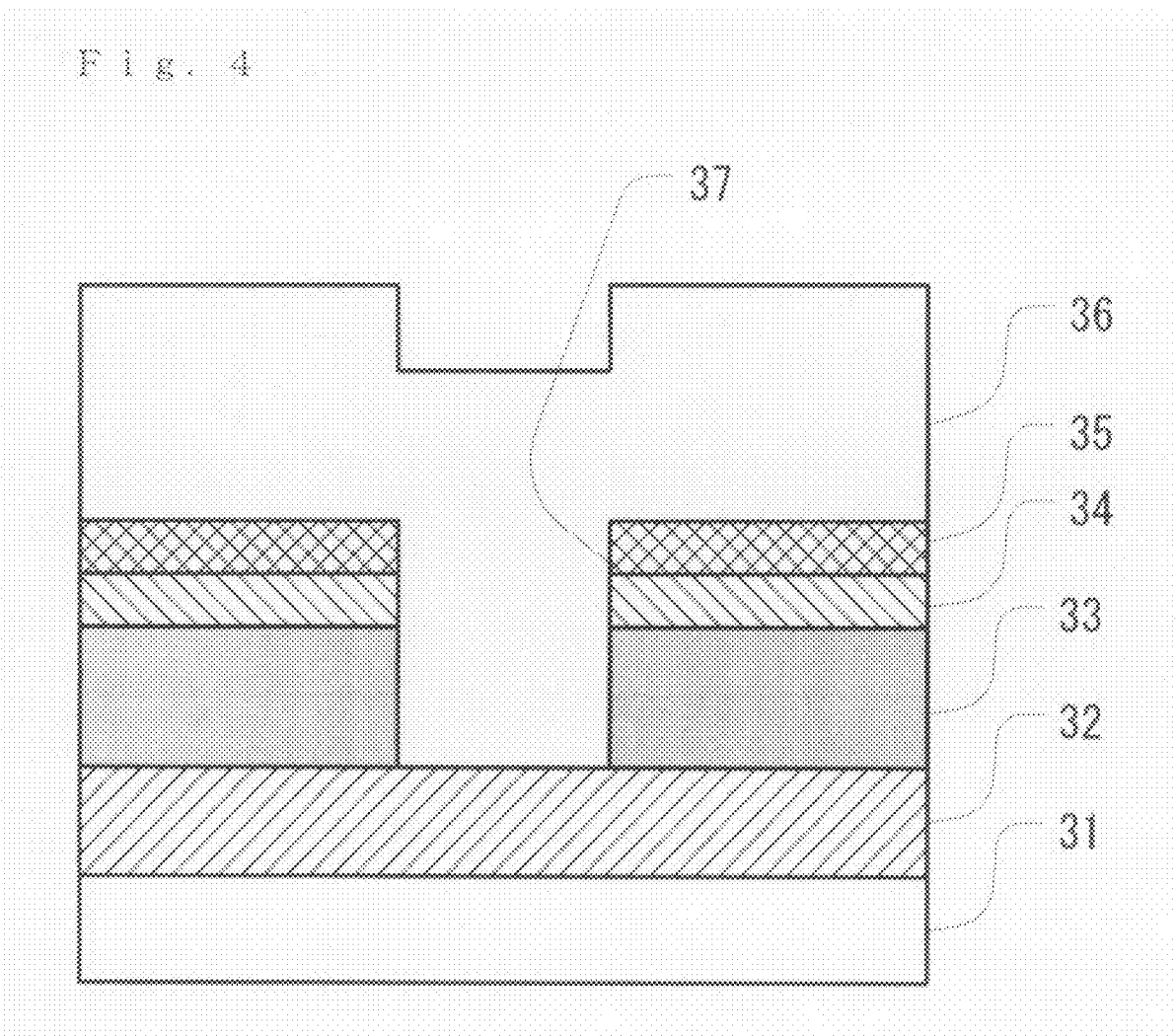
FIG. 4 is a diagram showing the structure of a wafer that has undergone polishing in an embodiment of the present invention.

A wafer having the structure shown in FIG. 4 was polished, and the polishing endpoint was detected by the method of the first working configuration of the present invention. The wafer shown in FIG. 4 was produced by laminating an oxidation film 32, a low-k film 33, a CAP layer 34, a Ta/TaN layer 35, and copper 36 in that order on the surface of a silicon substrate 31. A trench part 37 was formed in the low-k film 33, the CAP layer 34, and the Ta/TaN layer 35, and this trench part was filled in with the copper 36.

The CMP polishing apparatus used was an NPS3301 (manufactured by Nikon; NPS is a trademark). As is shown in FIG. 2, the NPS3301 allows the worked surface to be visually observed at all times, and is equipped with an instrument for detecting the step endpoint, above the worked surface. The instrument is designed to constantly monitor a peripheral strip 10 mm from the edge of the wafer during working.

Figure 5:
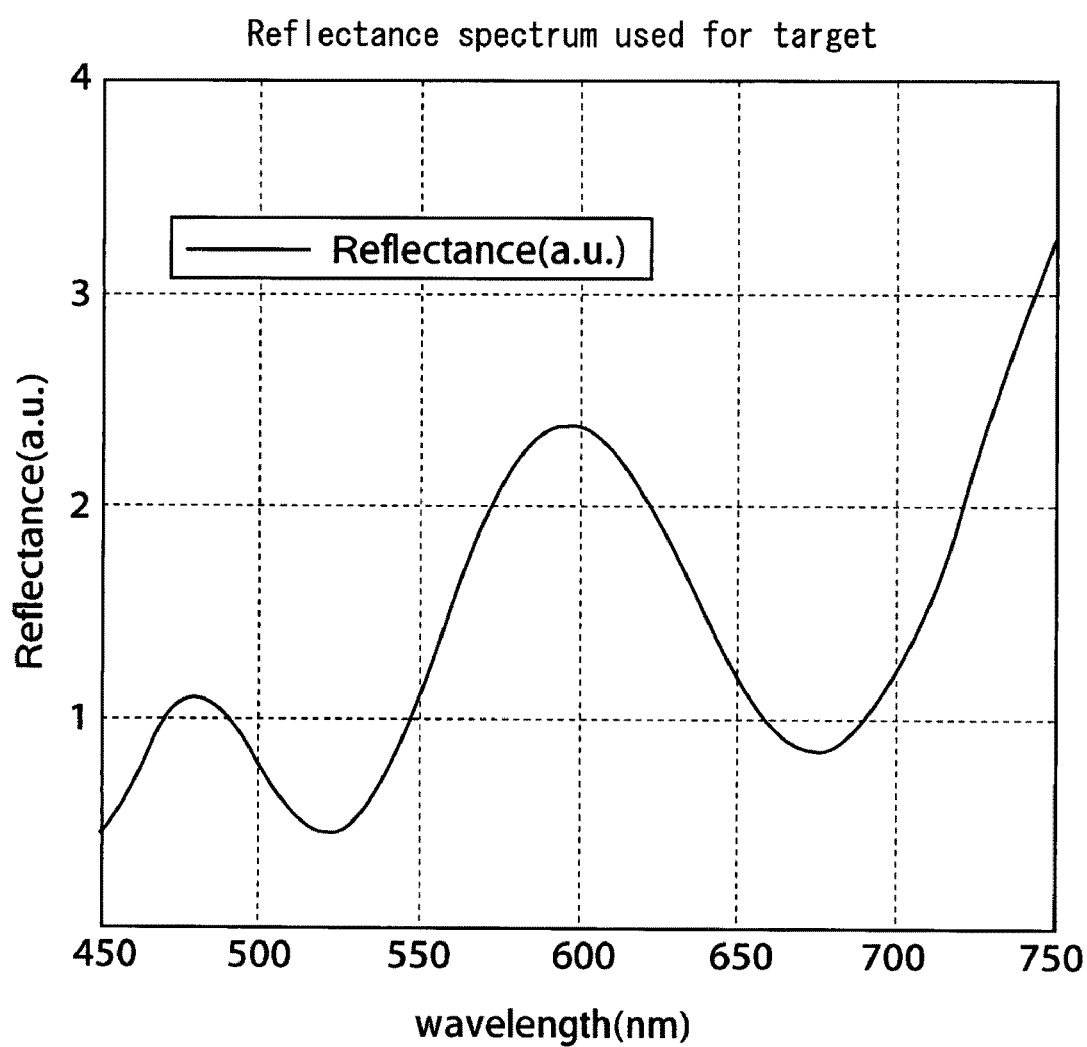
FIG. 5 is a diagram showing the target (reference) spectral reflectance spectrum obtained in a first embodiment of the present invention.
Figure 6:
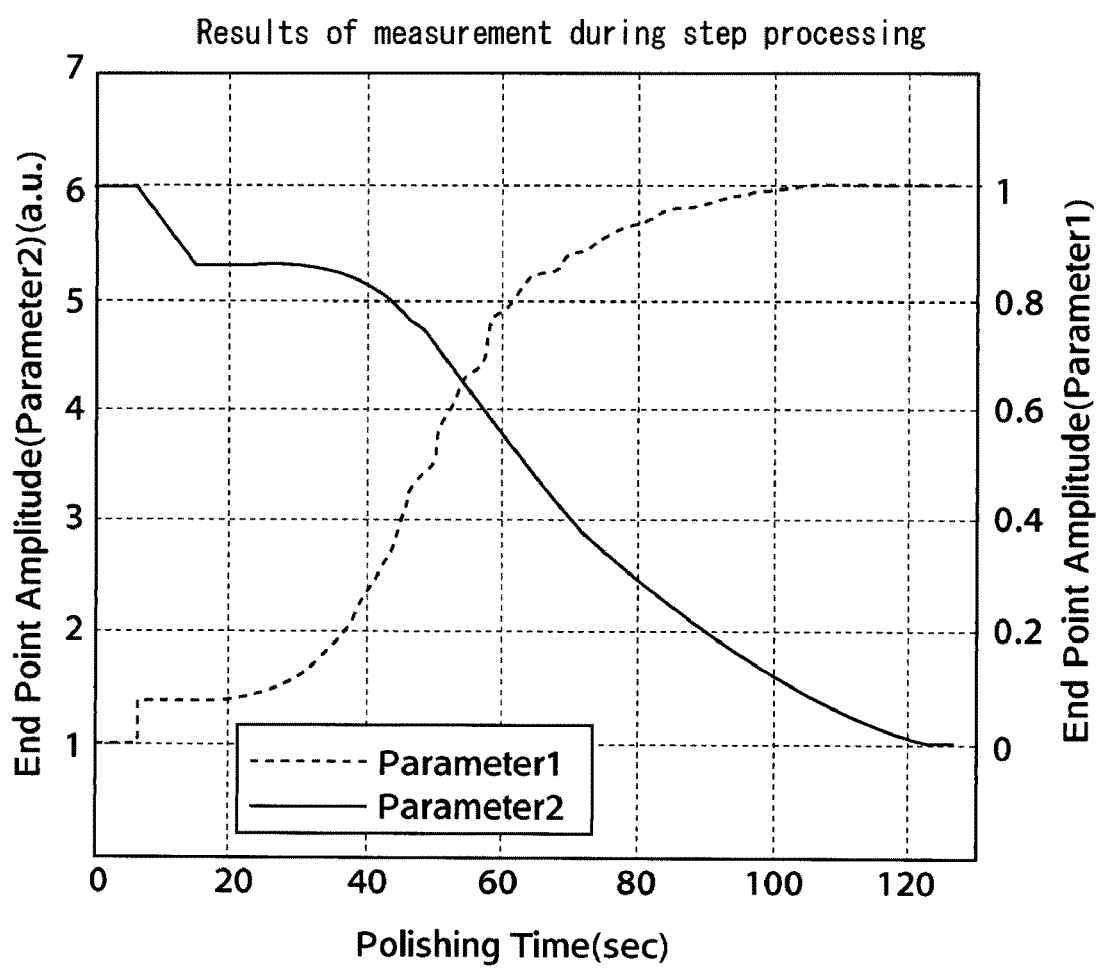
FIG. 6 is a diagram showing the transitions in parameter 1 and parameter 2 in the first embodiment of the present invention.
Figure 7:
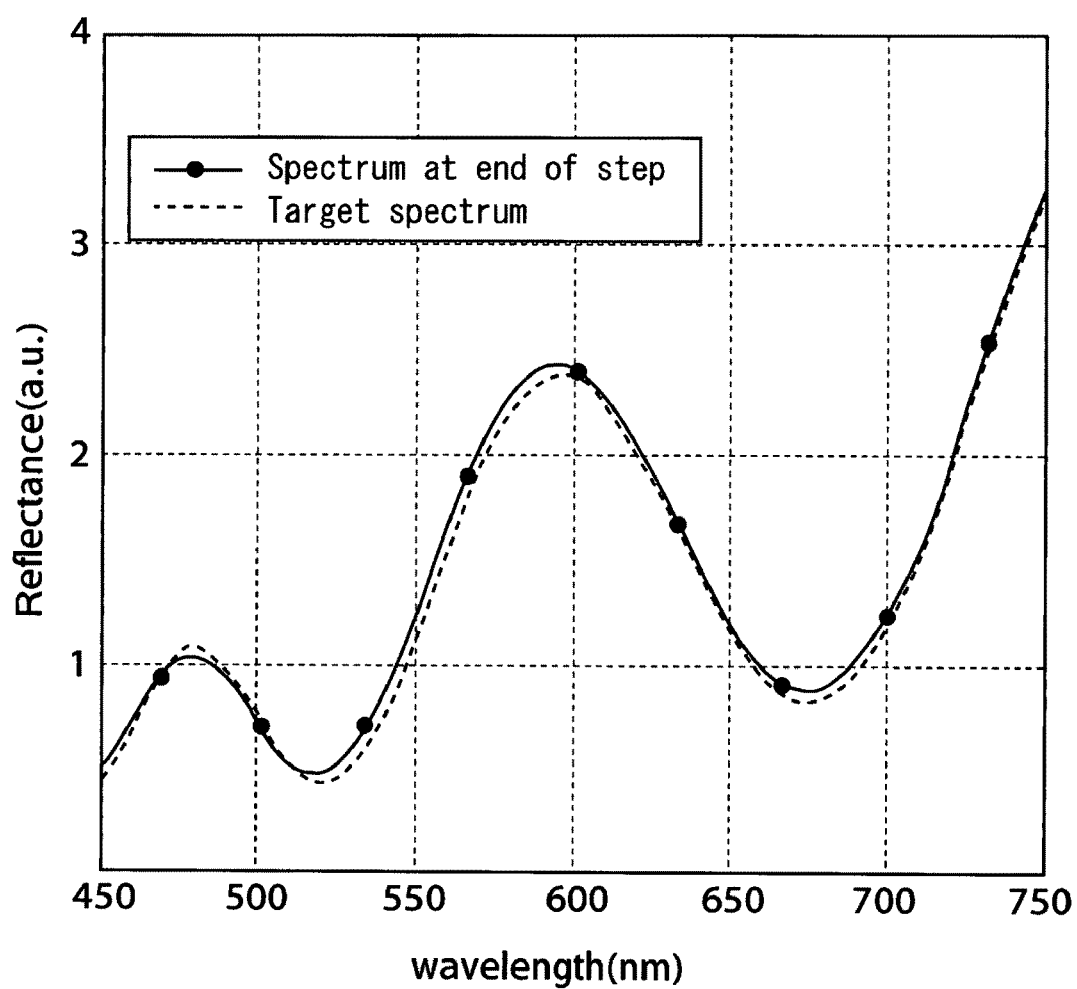
FIG. 7 is a diagram showing the target spectral reflectance spectrum and the spectral reflectance spectrum at the endpoint of the step in the first embodiment of the present invention.

To find the target (reference) spectral reflectance spectrum, a patterned wafer having the structure shown in FIG. 4 was polished. Following the endpoint determination of the Ta/TaN layer 35, additional polishing was performed until the remaining CAP layer film was 50 nm thick, and this point was seen as the polishing endpoint. FIG. 5 shows the relative values of the spectral reflectance spectrum in this case (target spectral reflectance spectrum). Another wafer having the structure shown in FIG. 4 was prepared, and polishing endpoint detection was performed by the method shown in the first working configuration. These results are shown in FIG. 6. The dashed line (parameter 1) in FIG. 6 indicates the correlation coefficient (relative value) of the reflectance spectrum observed during the step and the target. Furthermore, the solid line (parameter 2) is the product of calculating the first order differential of the target spectral reflectance spectrum and the first order differential of the spectral reflectance spectrum observed during the polishing step, finding the absolute values of the difference between the two at each wavelength, and calculating the sum thereof (relative value). It was concluded that when the value indicated by the dashed line was in a range exceeding 0.8, and the value indicated by the solid line was at its minimum, the polishing endpoint had been reached, and the CMP polishing was automatically halted. The remaining CAP layer at that point was approximately 50 nm thick, and it was possible to confirm the step endpoint in a state in which the film thickness was substantially the same as that in the target spectral reflectance spectrum. FIG. 7 shows the target spectral reflectance spectrum and the spectral reflectance spectrum at the step endpoint. As is clear from FIG. 7, the reflectance of both has substantially the same shape. These results confirmed that the step endpoint could be detected with good reproducibility from any remaining film of the wafer.

Embodiment 2

A wafer having the same structure as in Embodiment 1 was polished, and the endpoint of this polishing was detected. However, the thicknesses of the various layers of the wafer used here were different from those in Embodiment 1. The spectral reflectance spectrum at the polishing endpoint (target reflectance) was acquired under the polishing condition which is such that the polishing pressure is 1.5 psi. The holder speed in this case was 61 rpm, and the applied current value of the white LED was 10 (relative value). The applied current value of the white LED was automatically controlled so that the reflected light from the wafer would be in the optimal state.

Figure 8:
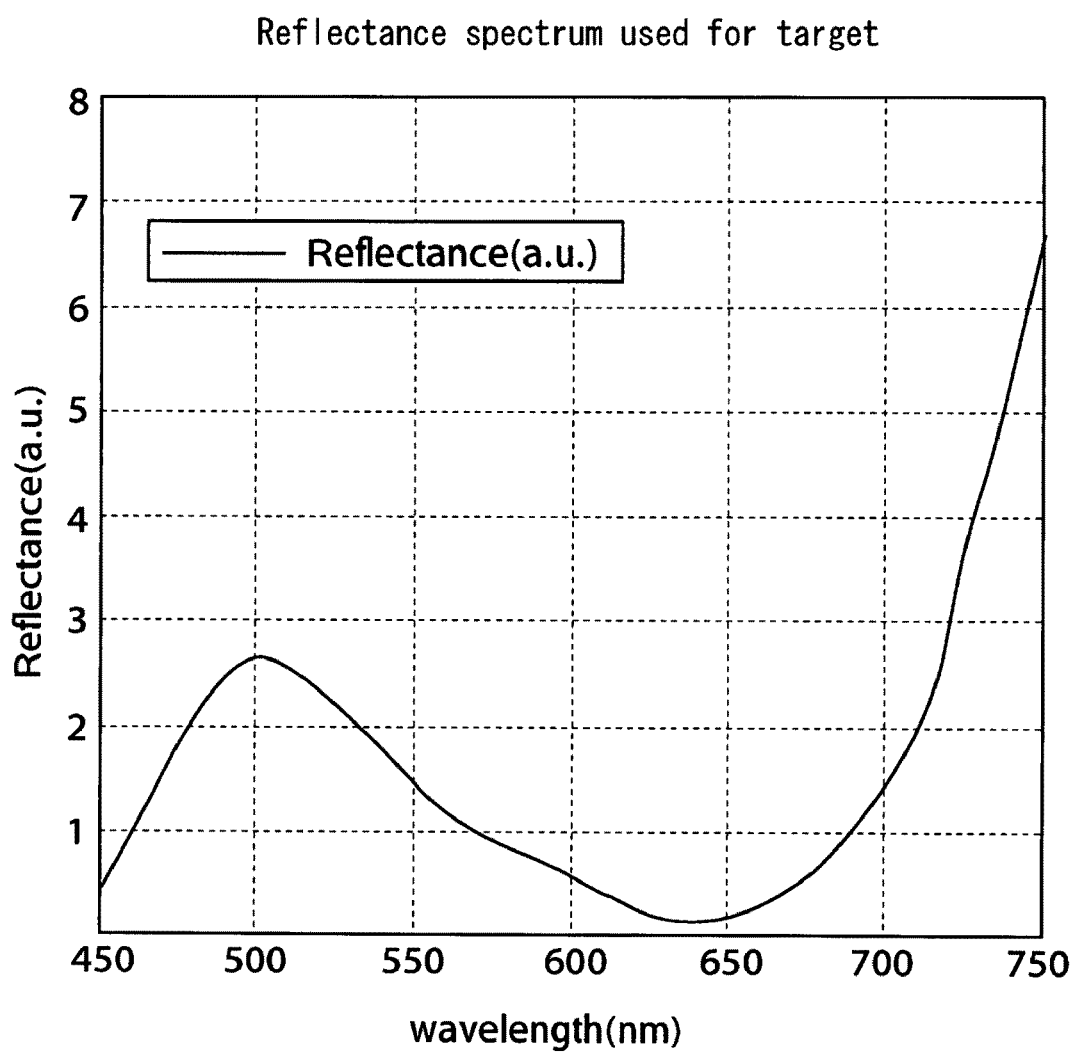
FIG. 8 is a diagram showing the spectral reflectance spectrum (target spectral reflectance spectrum) at the polishing endpoint in a second embodiment of the present invention.
Figure 9:
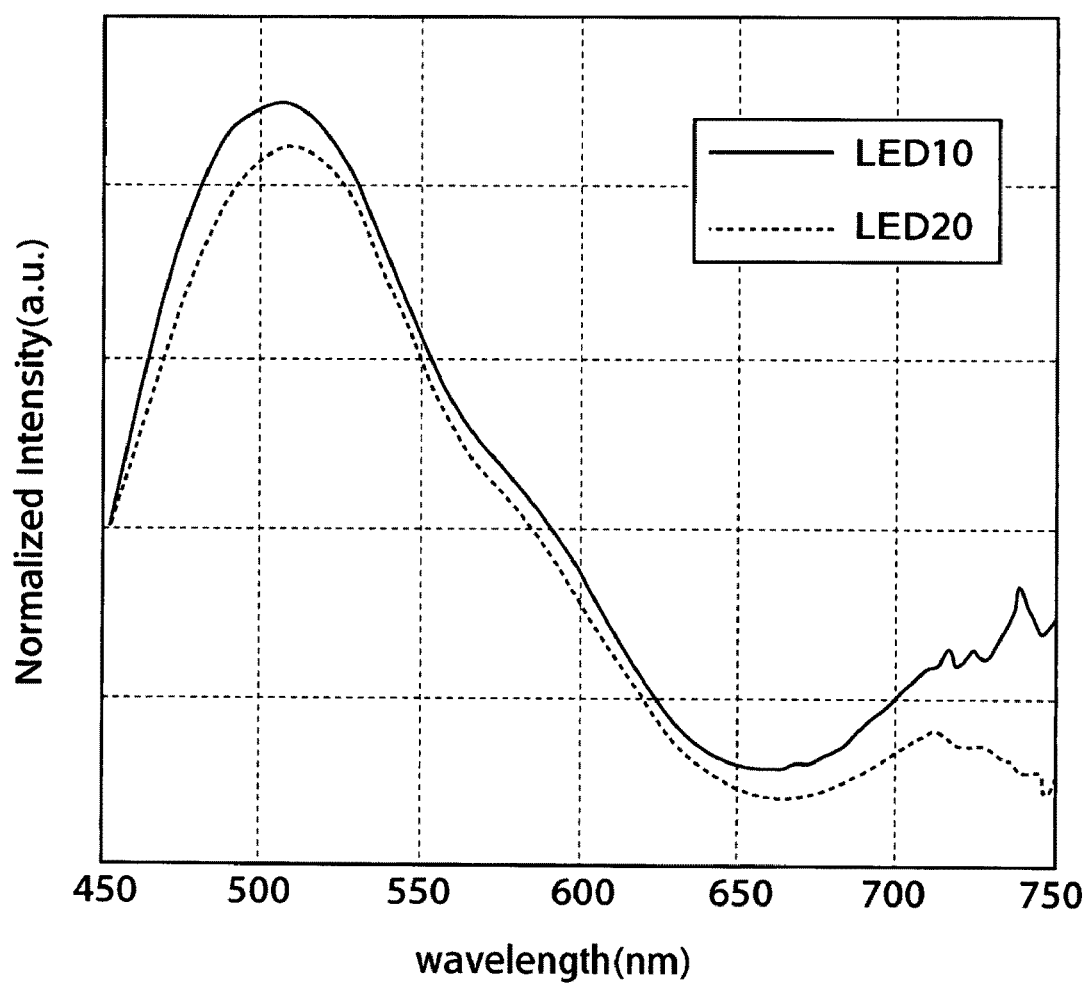
FIG. 9 is a diagram showing the changes in the emission spectrum distribution in a case where the current applied to the white LED is varied.

FIG. 8 shows the spectral reflectance spectrum (target spectral reflectance spectrum) at the polishing endpoint acquired under these conditions. Next, polishing was performed with the polishing pressure changed to 0.05 psi. This change in the polishing pressure was accompanied by a change in polishing conditions (holder speed). As a result, because of the change in the holder speed, the conditions for measuring the entire circumference of the wafer became different. Moreover, the state of turbulence caused by the slurry also changed, and the current value applied to the white LED became 20 (relative value). As a result, the emission characteristics of the white LED changed as shown in FIG. 9, and it was found that even though wafers having the same structure were polished, the spectral reflectance spectrum detected by the detector was different, so that the polishing endpoint could not be detected accurately. In view of this, the amount of light was adjusted by maintaining the current applied to the white LED at a constant value and inserting a variable ND filter.

Figure 10:
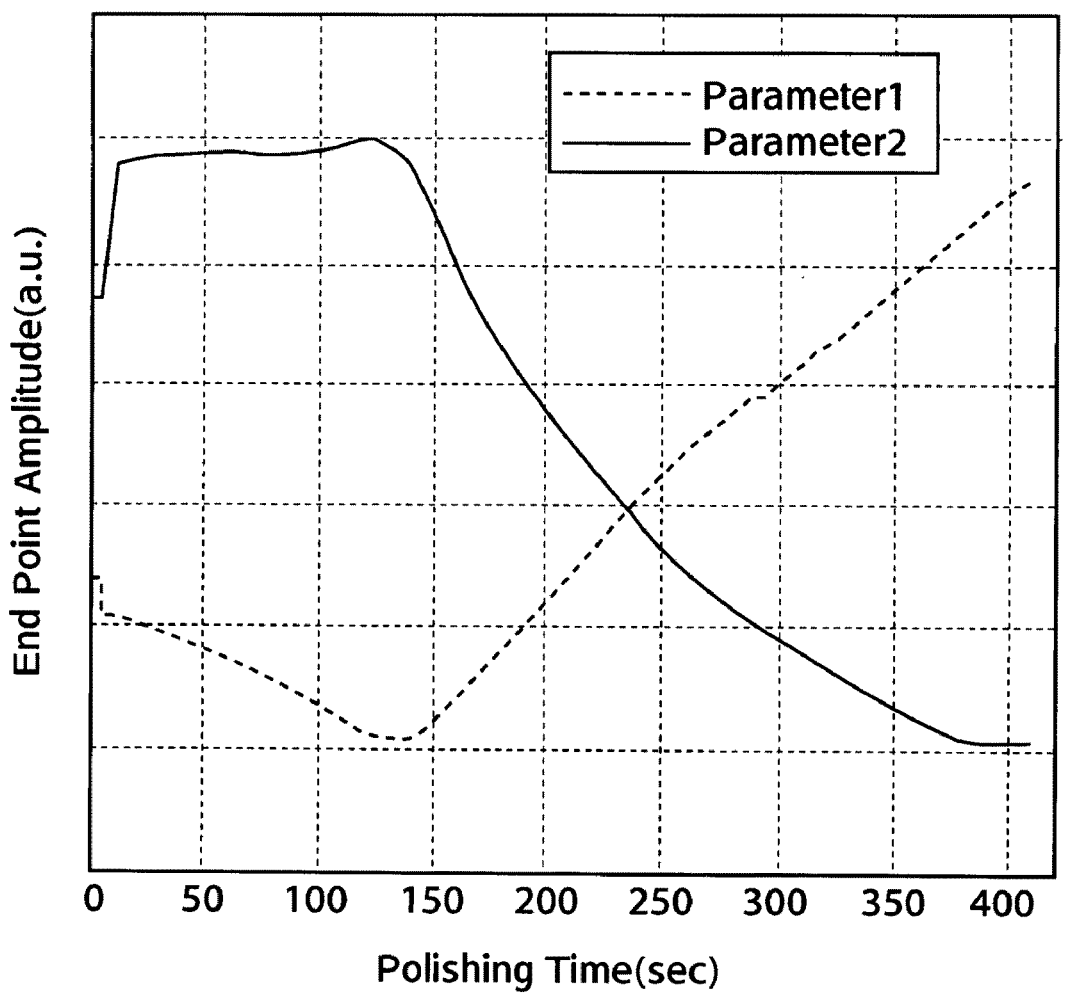
FIG. 10 is a diagram showing the manner in which parameter 1 and parameter 2 in the second embodiment of the present invention change.
Figure 11:
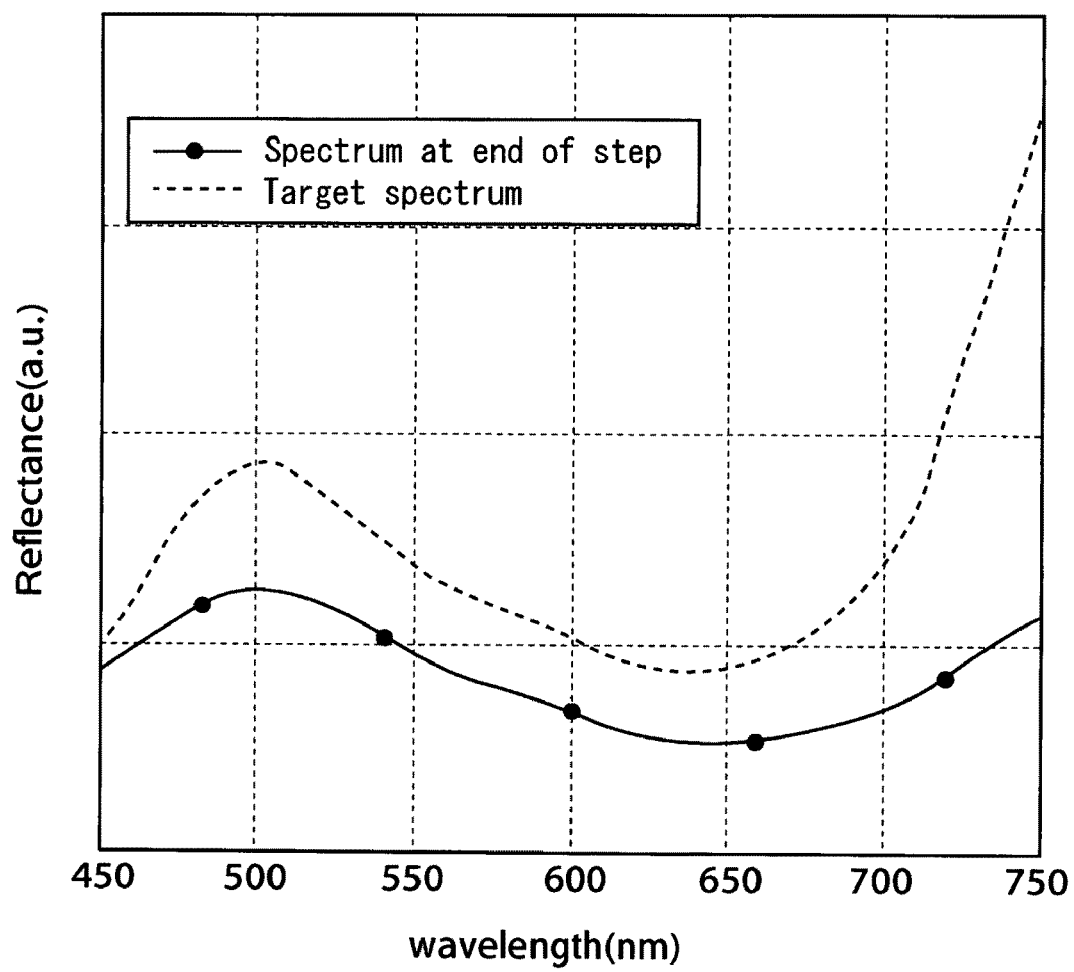
FIG. 11 is a diagram showing the spectral reflectance spectrum used as a reference (target spectral reflectance spectrum) and the spectral reflectance spectrum at the completion of the actual polishing step in the second embodiment of the present invention.

FIG. 10 shows the manner in which parameter 1 and parameter 2 (which respectively have the same meanings as those shown in FIG. 6) change when polishing endpoint detection was performed using the first working configuration by keeping the current applied to the white LED at a constant value and inserting a variable ND filter to adjust the amount of light. FIG. 11 shows the spectral reflectance spectrum serving as a reference (target spectrum) and the spectral reflectance spectrum at the completion of the actual polishing step. Even though the polishing pressure was changed, a spectral reflectance spectrum of the same shape was detected, and the same result was seen for the remaining wafer film following working.

The invention claimed is:

1. A method for detecting the polishing endpoint in a CMP polishing apparatus, comprising the following steps:
   (a) a step of finding in advance during CMP polishing the spectral reflectance spectrum of a reference wafer that has reached the polishing endpoint;
   (b) a step of finding the spectral reflectance spectrum of a sample wafer during CMP polishing, and finding a correlation coefficient with the spectral reflectance spectrum of the reference wafer that has reached the polishing endpoint found in step (a);
   (c) a step of finding, within the duration of CMP polishing, the sum of the absolute values of the difference at each wavelength, or the sum of the squares of the difference at each wavelength, between the first order differential with respect to the wavelength of the spectral reflectance spectrum found in step (a), and the first order differential with respect to the wavelength of the spectral reflectance spectrum found in step (b);
   (d) a step of determining the polishing endpoint to be the point at which the sum of the absolute values of the difference at each wavelength, or the sum of the squares of the difference at each wavelength, found in step (c) is at the minimum value within a range in which the correlation coefficient found in step (b) is equal to or greater than a specific threshold and;
   (e) a step of CMP polishing the sample wafer.

2. The method for detecting the polishing endpoint in a CMP polishing apparatus according to claim 1, wherein in step (c), smoothing is performed after the first order differentials are found, and these smoothed values are used in calculating the sum of the absolute values of the difference at each wavelength, or the sum of the squares of the difference at each wavelength.

3. A method for detecting the polishing endpoint in a CMP polishing apparatus, comprising the following steps:
   (a) a step of finding in advance during CMP polishing a plurality of spectral reflectance spectra of reference wafers undergoing polishing, along with the spectral reflectance spectrum of a reference wafer that has reached the polishing endpoint;
   (b) a step of finding the spectral reflectance spectrum of a sample wafer within the duration of CMP polishing, and finding a correlation coefficient between the spectral reflectance spectrum of the reference wafer that has reached the polishing endpoint found in step (a), and the spectral reflectance spectrum of the object of polishing undergoing the polishing step;
   (c) a step of finding, within the duration of CMP polishing, the sum of the absolute values of the difference at each wavelength, or the sum of the squares of the difference at each wavelength, between the first order differential with respect to the wavelength of the spectral reflectance spectrum of the reference wafer that has reached the polishing endpoint found in step (a), and the first order differential with respect to the wavelength of the spectral reflectance spectrum found in step (b);
   (d) a step of determining the polishing endpoint to be the point at which the correlation coefficient with the previously found spectral reflectance spectrum of the reference wafer that has reached the polishing endpoint becomes the highest out of the correlation coefficients found in step (b), and the sum of the absolute values of the difference at each wavelength, or the sum of the squares of the difference at each wavelength, found in step (c) is at the minimum value and;
   (e) a step of CMP polishing the sample wafer.

4. The method for detecting the polishing endpoint in a CMP polishing apparatus according to claim 3, wherein in step (c), smoothing is performed after the first order differentials are found, and these smoothed values are used in calculating the sum of the absolute values of the difference at each wavelength, or the sum of the squares of the difference at each wavelength.

5. The method for detecting the polishing endpoint in a CMP polishing apparatus according to any one of claims 1, 2, 3, and 4, wherein a white LED is used as the light source for measuring the spectral reflectance spectrum, the current applied to this white LED is controlled at a constant value, and the amount of irradiating light is controlled using a variable ND filter so that the amount of reflected light from the object of polishing will fall within a specific range.

6. The method for detecting the polishing endpoint in a CMP polishing apparatus according to any one of claims 1, 2, 3, and 4, wherein a white LED is used as the light source for measuring the spectral reflectance spectrum, the current applied to this white LED is controlled so that the amount of reflected light from a sample wafer will fall within a specific range, and the spectral reflectance spectrum of the object of polishing attributable to the change in the emission spectrum of the white LED due to the change in the current applied to the white LED is compensated on the basis of the relationship between the applied current and the emission spectrum of the white LED as determined ahead of time.

7. The method for detecting the polishing endpoint in a CMP polishing apparatus according to any one of claims, wherein the spectral reflectance spectrum is the average value or integrated value over one rotation of the object of polishing undergoing CMP polishing.

8. The method for detecting the polishing endpoint in a CMP polishing apparatus according to any one of claims 1, 2, 3, and 4, wherein the spectral reflectance spectrum of the object of polishing at a specific length of time prior to reaching the polishing endpoint is used instead of the spectral reflectance spectrum of the object of polishing that has reached the polishing endpoint.

9. The method for detecting the polishing endpoint in a CMP polishing apparatus according to any one of claims 1, 2, 3, and 4, wherein this method also has a polishing endpoint detection method comprising the following steps, and the polishing endpoint is determined to be the point at which the polishing endpoint is first detected in any of the polishing endpoint detection methods:
   (a) a step of performing over-polishing during CMP polishing after the polishing endpoint has been reached, and finding in advance the spectral reflectance spectrum of a reference wafer at one or a plurality of points during the over-polishing;
   (b) a step of finding the spectral reflectance spectrum of a sample wafer during CMP polishing, and finding a correlation coefficient with any of the spectral reflectance spectra of the reference wafer during over-polishing as found in step (a); and
   (c) a step of determining the polishing endpoint to be the point at which the correlation coefficient found in step (b) is equal to or greater than a specific threshold.

10. A method for detecting the polishing endpoint in a CMP polishing apparatus, comprising the following steps:
   (a) a step of finding in advance during CMP polishing the spectral reflectance spectrum of a reference wafer that has reached the polishing endpoint;
   (b) a step of finding the spectral reflectance spectrum of a sample wafer during CMP polishing;

(c) a step of finding, within the duration of CMP polishing, the sum of the absolute values of the difference at each wavelength, or the sum of the squares of the difference at each wavelength, between the first order differential with respect to the wavelength of the spectral reflectance spectrum found in step (a), and the first order differential with respect to the wavelength of the spectral reflectance spectrum found in step (b);

(d) a step of determining the polishing endpoint to be the point at which the sum of the absolute values of the difference at each wavelength, or the sum of the squares of the difference at each wavelength, found in step (c) becomes the minimum value and;

(e) a step of CMP polishing the sample wafer.

11. The method for detecting the polishing endpoint in a CMP polishing apparatus according to claim 10, wherein the method further includes a step of measuring polishing time and when it is detected that the polishing time exceeds a predetermined time before the polishing endpoint, steps (b), (c) and (d) are commenced.

12. A method for detecting the polishing endpoint in a CMP polishing apparatus, comprising the following steps:

(a) a step of finding in advance during CMP polishing the spectral reflectance spectrum of a reference wafer that has reached the polishing endpoint;

(b) a step of finding the spectral reflectance spectrum of a sample wafer during CMP polishing, and finding a correlation coefficient with the spectral reflectance spectrum of the reference wafer that has reached the polishing endpoint as found in step (a);

(c) a step of finding, within the duration of CMP polishing, the sum of the absolute values of the difference at each wavelength, or the sum of the squares of the difference at each wavelength, between the first order differential with respect to the wavelength of the spectral reflectance spectrum found in step (a), and the first order differential with respect to the wavelength of the spectral reflectance spectrum found in step (b), within a range in which the correlation coefficient found in step (b) is equal to or greater than a specific threshold;

(d) a step of determining the polishing endpoint to be the point at which the sum of the absolute values of the difference at each wavelength, or the sum of the squares of the difference at each wavelength, found in step (c) is at the minimum value and;

(e) a step of CMP polishing the sample wafer.

* * * * *